_United States Patent_ [19]

Hosoi et al.

[11] Patent Number: 5,599,504
[45] Date of Patent: Feb. 4, 1997

[54] APPARATUS FOR DETECTING DENATURATION OF NUCLEIC ACID

[75] Inventors: Shigeru Hosoi; Tadashi Fukami; Akihiko Tsuji, all of Hamamatsu, Japan

[73] Assignee: Hamamatsu Photonics K.K., Hamamatsu, Japan

[21] Appl. No.: 275,910

[22] Filed: Jul. 15, 1994

[30] Foreign Application Priority Data

Jul. 15, 1993 [JP] Japan .................................. 5-175730

[51] Int. Cl.⁶ ................................................ G01N 21/64
[52] U.S. Cl. ............... 422/82.08; 422/68.1; 422/82.05; 435/6; 435/91.2; 435/287.2; 435/288.7; 935/87
[58] Field of Search ................ 422/82.08, 68.1, 422/82.05; 436/55, 94; 435/6, 91.1, 91.2, 287.2, 288.7; 935/85–88

[56] References Cited

U.S. PATENT DOCUMENTS

| | | | |
|---|---|---|---|
| 4,743,535 | 5/1988 | Carrico | 435/6 |
| 5,175,273 | 12/1992 | Bischofberger | 536/27 |
| 5,326,692 | 7/1994 | Brinkley | 435/6 |
| 5,364,759 | 11/1994 | Caskey et al. | 435/6 |
| 5,401,847 | 3/1995 | Glazer et al. | 546/107 |

FOREIGN PATENT DOCUMENTS 9205448  4/1992  WIPO .

OTHER PUBLICATIONS

Morrison et al. Anal. Biochem., 183, 231–244 (1989).
Hiyoshi, Anal. Biochem., 221, 306–311 (1994).
Morrison et al., Biochemistry, (1993), 32, 3095–3104.
Verpy, Proc. Nat. Acad. Sci, USA, 91, 1873–1877, (1994).
Freifelder, Physical Biochemistry: Applications to Biochemistry and Molecular Biology, 2nd Edition, W. H. Freeman and Comany (New York) pp. 19–20.

_Primary Examiner_—Jill Warden
_Assistant Examiner_—Jan M. Ludlow
_Attorney, Agent, or Firm_—Cushman Darby & Cushman of Pillsbury Madison & Sutro LLP

[57] ABSTRACT

An apparatus for detecting denaturation of a nucleic acid, including: denaturation condition controlling element for controlling condition of denaturation under which a double-strand nucleic acid is separated into a first single-strand nucleic acid and a second single-strand nucleic acid; excitation light irradiation source for irradiating the double-strand nucleic acid before denaturation, and the first single-strand nucleic acid and second single-strand nucleic acid after the denaturation; fluorescence detection monitor for detecting fluorescence emission based on the excitation light irradiation; and processing element for receiving, storing and processing a signal supplied from the fluorescence detection monitor.

11 Claims, 10 Drawing Sheets

BEFORE DENATURATION (DOUBLE-STRAND)

DURING DENATURATION (PARTIALLY DOUBLE-STRAND)

AFTER DENATURATION

Fig. 9B

— : NORMAL
-- : ABNORMAL

APPARATUS FOR DETECTING DENATURATION OF NUCLEIC ACID

BACKGROUND OF THE INVENTION

1. Field of the Invention

The present invention relates to structural analysis of nucleic acids, and more particularly to an apparatus for detecting denaturation of nucleic acids.

2. Related Background Art

Much attention has been attracted to techniques for detecting and measuring in denaturation of nucleic acids (DNA, RNA, and hybrid thereof) with accuracy which substantially resolves a difference in the denaturation conditions based on single base (or single base-pair) substitution, deletion or addition.

As a method capable of detecting slight differences such as the above-mentioned single base alteration between homologous double-strand nucleic acids, there has been proposed a method called "denaturing gradient gel electrophoresis method" (S. G. Fischer and L. S. Lerman: Proc. Natl. Acid. Sci. U.S.A., Vol. 80, pp. 1579–1583, March 1983). In this method, a double-strand nucleic acid to be measured is first amplified using an ordinary technique such as polymerase chain reaction (hereinafter, referred to as "PCR method"). Then, the resultant double-strand nucleic acid is charged into a gel carrier (or gel support), and the double-strand nucleic acid is subjected to electrophoresis under a gradient of a denaturation condition (such as temperature or hydrogen ion concentration (pH)) which is spatially provided across the gel carrier. In this measurement, it is possible to simultaneously subject a control double-strand nucleic acid functioning as a reference (or standard) together with the double-strand nucleic acid to be measured so as to observe a difference in the denaturation condition between these two species of the double-strand nucleic acids (i.e., the double-strand nucleic acid to be measured and the reference double-strand nucleic acid).

Figure 9A:
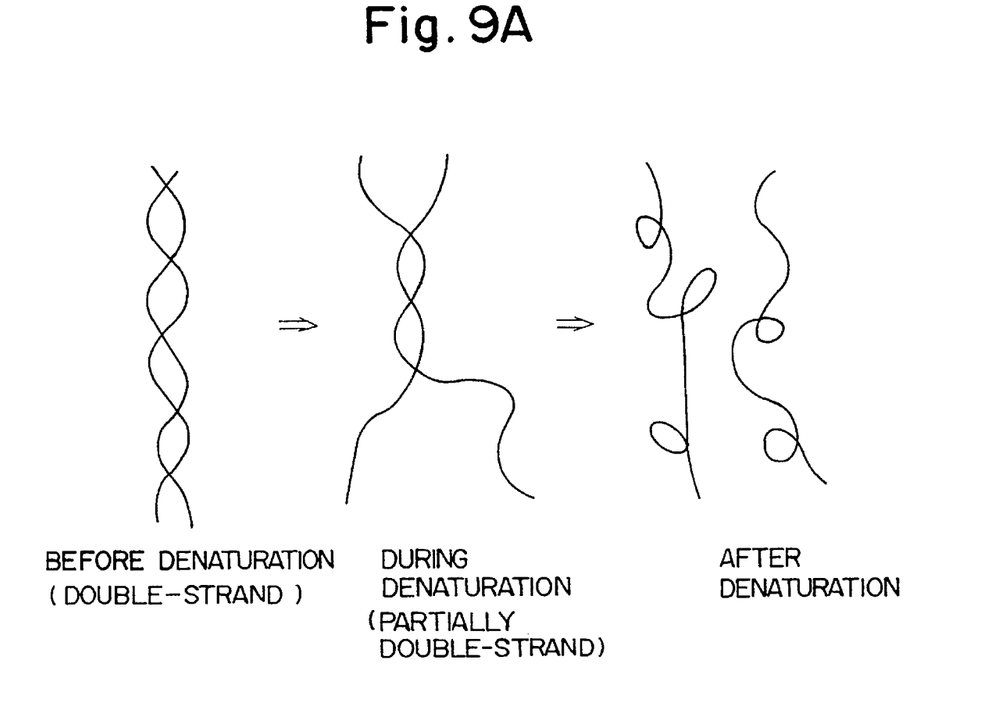
FIGS. 9A and 9B are schematic views for illustrating a conventional method of detecting the denaturation of a nucleic acid.
Figure 9B:
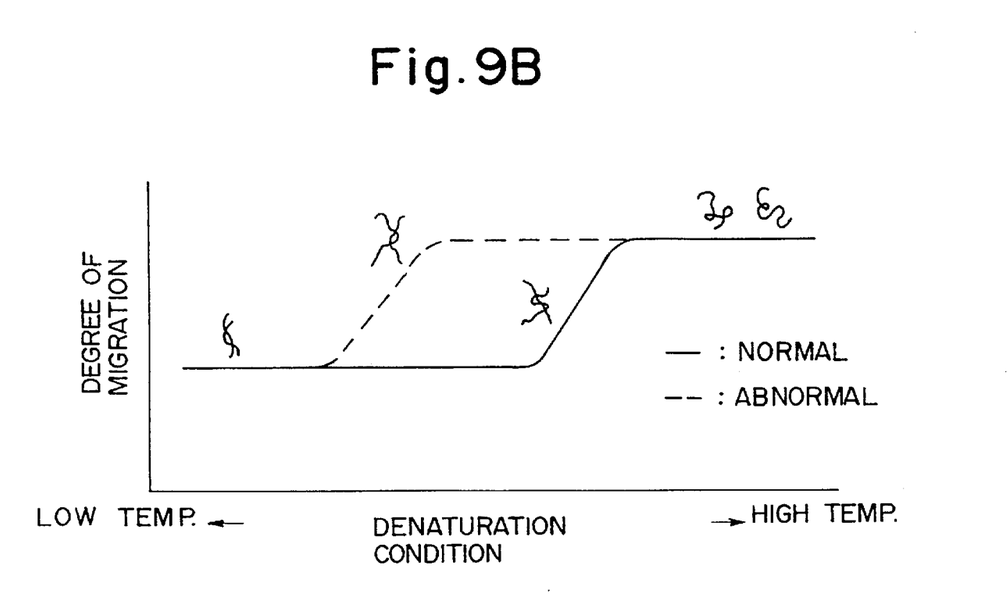

FIGS. 9A and 9B are schematic diagrams illustrating the above-mentioned conventional method for detecting the denaturation of a nucleic acid. For example, FIG. 9A relates to a case wherein temperature is selected as a denaturation condition, and schematically shows a state wherein a nucleic acid is denatured on the basis of temperature increase. In general, a double-strand nucleic acid is denatured when the ambient temperature is elevated to a predetermined value. The temperature at which a double-strand nucleic acid is denatured (denaturation temperature) depends on the composition of bases constituting the double-strand nucleic acid. A double-strand nucleic acid comprising a specific single-strand nucleic acid and another single-strand nucleic acid binding thereto which is completely complementary to the former single-strand nucleic acid, has a denaturation temperature higher than that of a double-strand nucleic acid comprising the above-mentioned specific single-strand nucleic acid and another single-strand nucleic acid binding thereto which is substantially (and not completely) complementary to the former single-strand nucleic acid.

Conventional apparatuses for detecting denaturation of a nucleic acid utilize such a phenomenon, and conduct gel electrophoresis while spatially providing a gradient of a denaturation condition in the gel carrier to be used for the electrophoresis.

FIG. 9B shows results of measurement relating to a case of a double-strand nucleic acid sample comprising a specific strand and another strand which is substantially complementary to the specific strand. As shown in FIG. 9B, when two denaturation points (i.e., points at which denaturation occurs) are present, one double-strand nucleic acid showing a denaturation condition of a lower temperature is the double-strand nucleic acid to be measured, and the other double-strand nucleic acid showing a higher temperature denaturation is the reference double-strand nucleic acid.

However, in the above-mentioned denaturation detection of a nucleic acid utilizing the conventional denaturing gradient gel electrophoresis method, it is necessary to subject the sample nucleic acid to electrophoresis in a gel across which a gradient or change in denaturation condition (temperature or pH) is provided. Accordingly, such a conventional denaturation detection method is troublesome or tedious. More specifically, the conventional method consumes a long period of time corresponding to several tens of minutes to several hours, while such a period of time depends on the molecular weight of the sample nucleic acid.

In addition, the sensitivity of detection of the nucleic acid denaturation by the conventional denaturing gradient gel electrophoresis method depends on the stability of the system to be used for such a purpose, the accuracy in the control of the denaturation condition such as degree of gradient to be provided to the gel, or the accuracy in the control of the condition for electrophoresis. However, it is difficult to improve the accuracy in the control of these conditions as compared with those accomplished at the present stage. Accordingly, there has been posed a problem such that further improvement is difficult with respect to the sensitivity and accuracy (or precision) of the denaturation detection.

SUMMARY OF THE INVENTION

An object of the present invention is to provide an apparatus for detecting the denaturation of a nucleic acid which has solved the above-mentioned problems encountered in the conventional apparatus.

Another object of the present invention is to provide an apparatus for detecting the denaturation of a nucleic acid which is capable of rapidly detecting the denaturation of a nucleic acid with high accuracy.

According to the present invention, there is provided an apparatus for detecting denaturation of a nucleic acid, comprising:

denaturation condition controlling means for controlling a condition of denaturation under which a double-strand nucleic acid is separated into a first single-strand nucleic acid and a second single-strand nucleic acid, the first single-strand nucleic acid comprises a base provided with a first label molecule, the second single-strand nucleic acid having a base sequence complementary to or substantially complementary to the first single-strand nucleic acid and comprising a base provided with a second label molecule which is capable of causing energy transfer between itself and the first label molecule located within a predetermined distance, the double-strand nucleic acid comprising the first single-strand nucleic acid and the second single-strand nucleic acid binding to the first single-strand nucleic acid;

excitation light irradiation means for emitting excitation light having a predetermined wavelength to irradiate the double-strand nucleic acid before denaturation, and the first single-strand nucleic acid and second single-strand nucleic acid after the denaturation, with the excitation light;

fluorescence detection means for detecting fluorescence emission which is based on the excitation light irradiation and is capable of being changed depending on a change in the amount of energy transfer between the first label molecule and the second label molecule; and processing means for receiving, storing and processing a signal supplied from the fluorescence detection means;

whereby the fluorescence emitted from the nucleic acid is observed while changing the denaturation condition by the denaturation condition controlling means, and a denaturation point (denaturation critical condition) is determined on the basis of the change in the fluorescence emission in response to the change in the denaturation condition.

The present invention also provides an apparatus for detecting denaturation of a nucleic acid which further comprises nucleic acid amplifying means for preparing a double-strand nucleic acid to be examined.

More specifically, the present invention also provides an apparatus for detecting denaturation of a nucleic acid, comprising:

first nucleic acid amplifying means for separating a predetermined site of a first double-strand nucleic acid to be examined into a first single-strand nucleic acid and a second single-strand nucleic acid to produce a large number of a third single-strand nucleic acid and a fourth single-strand nucleic acid, the third single-strand nucleic acid comprising a base or nucleotide provided with a first label molecule and having a base sequence complementary to that of the first single-strand nucleic acid, the fourth single-strand nucleic acid having a base sequence complementary to that of the second single-strand nucleic acid;

second nucleic acid amplifying means for separating a predetermined site of a second double-strand nucleic acid as a reference, which is the same or substantially the same as the first double-strand nucleic acid, into a fifth single-strand nucleic acid which is the same or substantially the same as the first single-strand nucleic acid, and a sixth single-strand nucleic acid which is the same as or substantially the same as the second single-strand nucleic acid, to produce a large number of a seventh single-strand nucleic acid and an eighth single-strand nucleic acid; the seventh single-strand nucleic acid comprising a base or nucleotide provided with a second label molecule which is capable of causing energy transfer between itself and the first label molecule located within a predetermined distance, and having a base sequence complementary to that of the fifth single-strand nucleic acid; the eighth single-strand nucleic acid having a base sequence complementary to that of the sixth single-strand nucleic acid;

nucleic acid mixing means for mixing the third single-strand nucleic acid and the eighth single-strand nucleic acid after the extraction thereof to produce a third double-strand or partially double-strand nucleic acid;

denaturation condition controlling means for controlling environment for denaturation under which the third double-strand nucleic acid is separated into the third single-strand nucleic acid and the eighth single-strand nucleic acid;

excitation light irradiation means for emitting excitation light having a predetermined wavelength to irradiate the third double-strand nucleic acid before denaturation, and the third single-strand nucleic acid and eighth single-strand nucleic acid after the denaturation, with the excitation light;

fluorescence detection means for detecting fluorescence emission based on the excitation light irradiation; and processing means for receiving, storing and processing a signal supplied from the fluorescence detection means;

whereby the fluorescence emitted from the nucleic acid is observed while changing the denaturation condition by the denaturation condition controlling means to measure the denaturation condition of the third double-strand nucleic acid.

In the above-mentioned apparatus for detecting denaturation of a nucleic acid according to the present invention, a double-strand nucleic acid to be subjected to denaturation measurement may be prepared by hybridizing a single-strand nucleic acid comprising a base or nucleotide labeled with an energy donor, with a single-strand nucleic acid comprising a base or nucleotide labeled with an energy acceptor and having a base sequence complementary to the former single-strand nucleic acid, and fluorescence having a predetermined wavelength emitted on the basis of the irradiation of the double-strand nucleic acid with excitation light is detected and measured. In the present invention, there may be provided a difference in fluorescence characteristic such as wavelength-intensity distribution of the emitted fluorescence or lifetime of the emitted fluorescence, on the basis of a difference between a case wherein energy is transferred from the energy donor to the energy acceptor in a double-strand state, and a case wherein substantially no energy is transferred from the energy donor to the energy acceptor since the double-strand nucleic acid is denatured into a single-strand state.

The apparatus for detecting denaturation of a nucleic acid according to the present invention may measure a characteristic value of the emitted fluorescence while controlling the denaturation condition of a double-strand nucleic acid, and may detect a change in the characteristic of the fluorescence emitted from the nucleic acid, thereby to recognize the denaturation of the double-strand nucleic acid and measure a predetermined value of the denaturation condition of the double-strand nucleic acid to be measured.

More specifically, in the first apparatus for detecting denaturation of a nucleic acid according to the present invention, a double-strand nucleic acid to be measured, which has been prepared in advance and comprises a single-strand nucleic acid including a base labeled with a fluorescence energy donor, and a single-strand nucleic acid including a base labeled with an energy acceptor and binding to the former single-strand nucleic acid, is disposed or placed at a measuring point where the denaturation condition (such as temperature) may be controlled. An initial value of the denaturation condition is set at a predetermined value under which no denaturation will occur. Excitation light irradiation is conducted in this state to measure the fluorescence emitted from the sample. At this time, the quantity or amount to be measured may be: (1) the quantity of characteristic fluorescence emitted from the energy acceptor, (2) the quantity of characteristic fluorescence emitted from the energy donor, or (3) lifetime of fluorescence emitted from the energy donor.

Subsequently, the quantity to be measured is measured while changing the denaturation condition under the control of a processing unit, thereby to store the quantity to be measured at each of the denaturation condition values. After the measurement, denaturation point (denaturation critical condition) may be determined by utilizing at least one selected from: the degree of a decrease in the characteristic fluorescence emitted from the energy acceptor after the denaturation in a case where the quantity of the characteristic fluorescence emitted from the energy acceptor is measured; the degree of an increase in the characteristic fluorescence emitted from the energy donor in a case where the quantity of the characteristic fluorescence emitted from the energy donor is measured; and the degree of a change in the lifetime of fluorescence emitted from the energy donor in a case where the lifetime of the fluorescence is measured.

In the second apparatus for detecting denaturation of a nucleic acid according to the present invention, denaturation may be detected in a nucleic acid comprising a single-strand nucleic acid to be examined and a reference single-strand nucleic acid binding to the former nucleic acid, by utilizing a nucleic acid sample to be examined and a reference nucleic acid as starting materials. In this apparatus, one of the two species of the nucleic acids (i.e., reference nucleic acid sample and nucleic acid sample to be examined) is subjected to PCR amplification by using a base labeled with an energy donor molecule (or, is subjected to PCR amplification and then subjected to polymerization by using a base labeled with an energy donor molecule), and the other of the two species of the nucleic acids is subjected to PCR amplification by using a base labeled with an energy donor molecule (or, is subjected to PCR amplification and then subjected to polymerization by using a base labeled with an energy donor molecule). From the thus amplified nucleic acids, single-strand nucleic acids, which are complementary to each other, are separately extracted or separated and then mixed to prepare a nucleic acid to be measured.

Subsequently, a denaturation point of the thus prepared nucleic acid to be measured may be determined by subjecting the nucleic acid to a measurement procedure in a similar manner as in the above-mentioned first apparatus for detecting denaturation of a nucleic acid.

Further objects and advantages of the present invention will be apparent from the description of the preferred embodiments with the accompanying drawings.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

Prior to the description of preferred embodiments of the present invention, there is described an outline of the measurement principle in the apparatus for detecting denaturation of a nucleic acid according to the present invention.

Figure 1A:
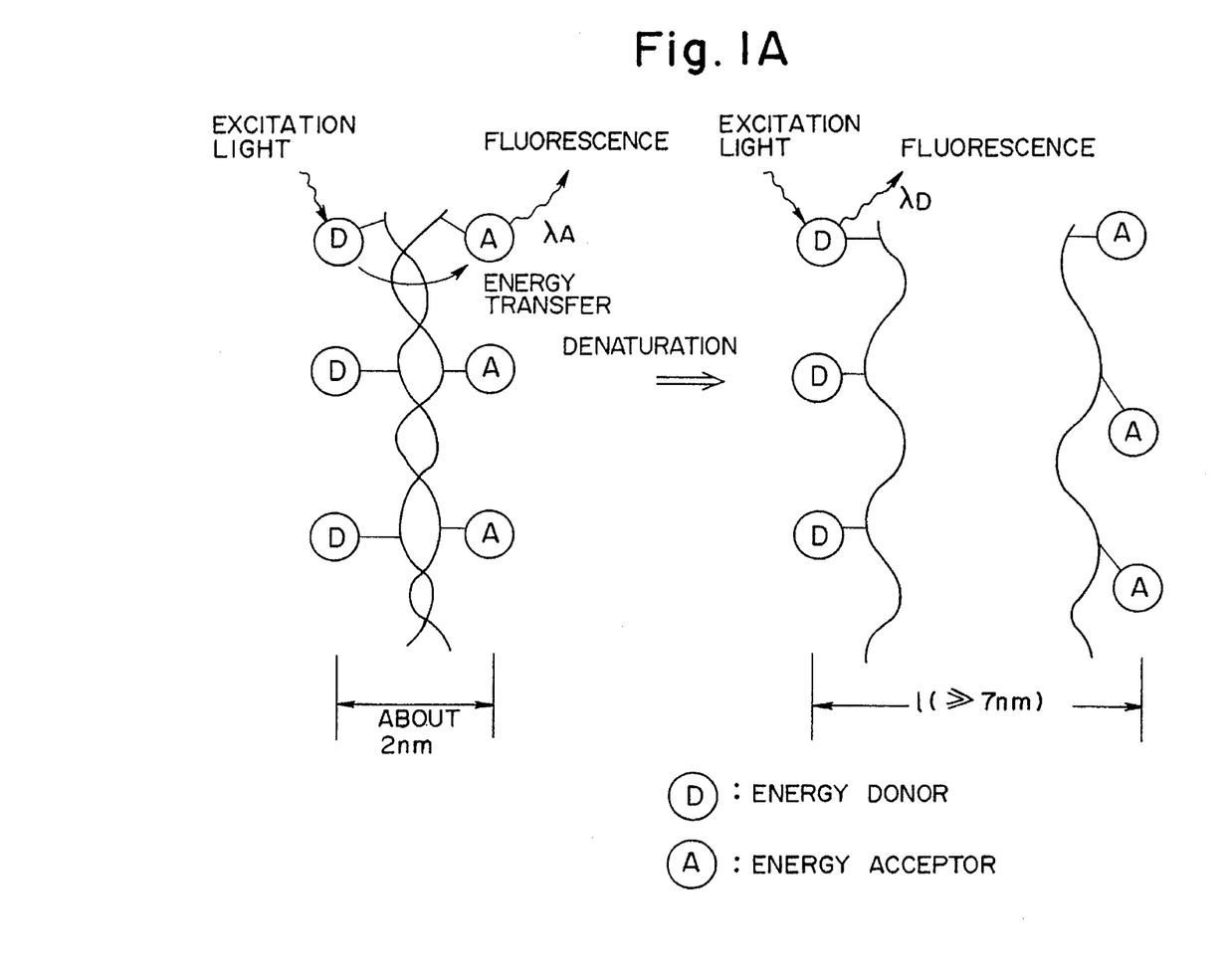
FIGS. 1A and 1B are schematic views for illustrating an energy transfer phenomenon to be utilized in an apparatus for detecting denaturation of a nucleic acid according to the present invention.

FIGS. 1A and 1B are schematic views for illustrating a phenomenon which is utilized for detecting the denaturation in a nucleic acid in the apparatus according to the present invention. As a fluorescent molecule capable of labeling or binding to the bases constituting a nucleic acid, there is known a combination of two species of fluorescent molecules which is capable of causing energy transfer when the distance between the two species of fluorescent molecules is 7 nm or smaller (L. Stryer: Ann. Rev. Biochem. 1978, vol.47, pp819–846). In addition, when a double-strand nucleic acid is formed while providing an energy donor to one single-strand nucleic acid and providing an energy acceptor to the other single-strand nucleic acid, it is possible to form a pair in which the distance between the energy donor (D) and the energy acceptor (A) is approximately 2 nm in the double-strand nucleic acid state as shown in FIG. 1A. In such a case, the average distance between the separated single-strand nucleic acids (after the denaturation of the double-strand nucleic acid) becomes much larger than 7 nm (i.e., the average distance capable of causing energy transfer between the single-strand nucleic acids constituting a double-strand nucleic acid).

When excitation light capable of causing a single energy donor to emit fluorescence is supplied to the above-mentioned double-strand nucleic acid or single-strand nucleic acid, the following phenomenon may occur.

(1) In the case of a double-strand state before denaturation, energy is transferred from the energy donor supplied with the excitation light to the energy acceptor, and the energy acceptor emits fluorescence having a wavelength of $\lambda_A$ (hereinafter, such fluorescence is referred to as "$\lambda_A$ fluorescence").

(2) In the case of a single-strand state after the denaturation, energy is not substantially transferred from the energy donor to the energy acceptor, and therefore only the energy donor emits fluorescence having a wavelength of $\lambda_D$ (hereinafter, such fluorescence is referred to as "$\lambda_D$ fluorescence").

Figure 1B:
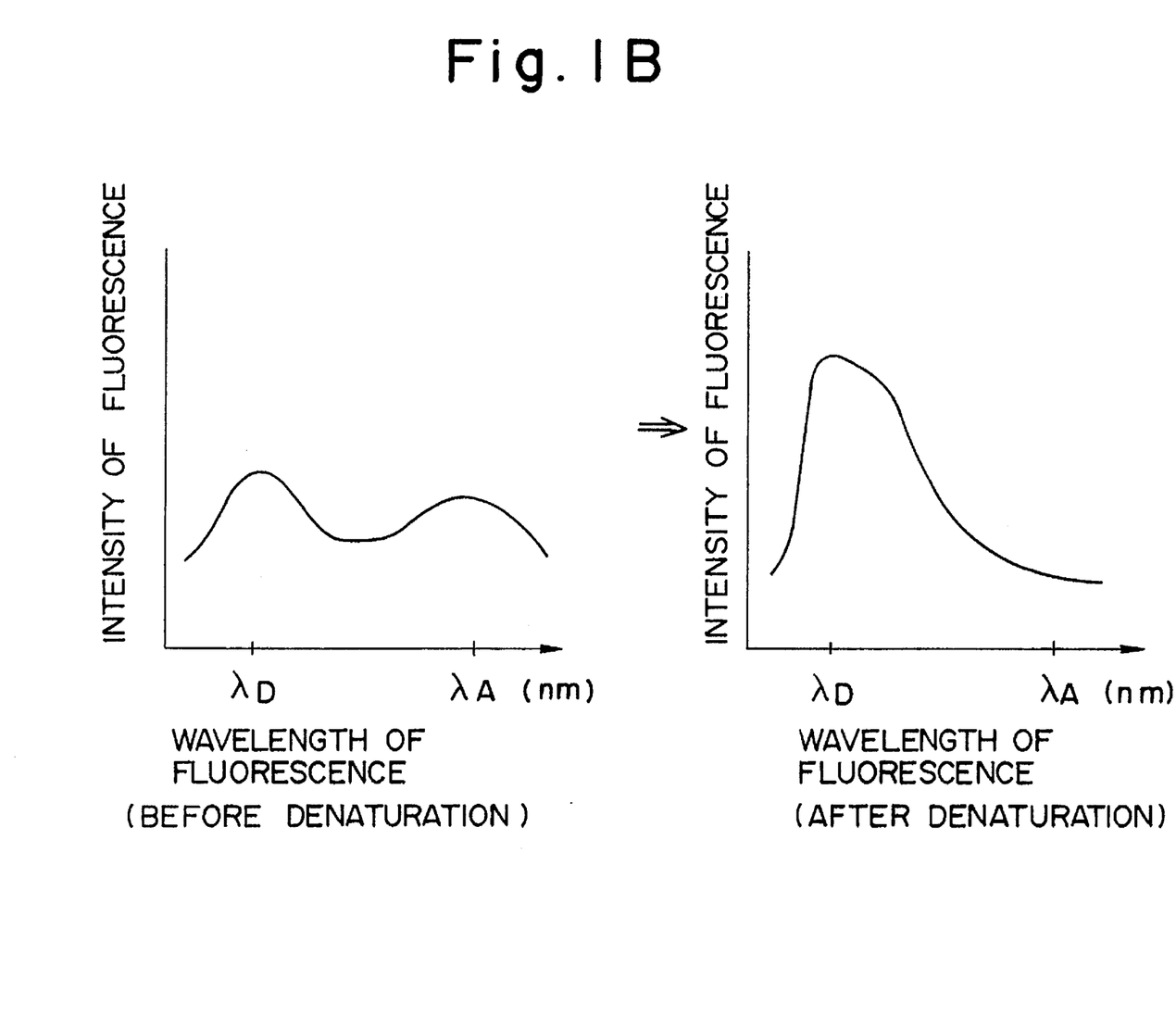

FIG. 1B shows an intensity-wavelength distribution of the fluorescence emitted in a case where excitation light is supplied to the double-strand nucleic acid state before denaturation, and an intensity-wavelength distribution of the fluorescence emitted in a case where excitation light is supplied to the single-strand nucleic acid state after the denaturation. As shown in FIG. 1B, when the intensities of the fluorescence before and after the denaturation are compared with each other, the intensity of the $\lambda_A$ fluorescence is decreased after the denaturation while the intensity of the $\lambda_D$ fluorescence is increased after the denaturation. In addition, while not shown in FIG. 1B, the lifetime of the $\lambda_D$ fluorescence is changed before and after the denaturation.

The apparatus for detecting denaturation of a nucleic acid according to the present invention is an apparatus for measuring a difference in the characteristic of the fluorescence emission before and after the denaturation as described above, thereby to detect the denaturation of a nucleic acid.

Hereinbelow, preferred embodiments of the present invention will be described with reference to the accompanying drawings. In these drawings, substantially the same or corresponding elements or components are denoted by the same or similar reference numerals, and redundant description thereof is omitted in the description relating to the drawings.

(First Embodiment)

Figure 2:
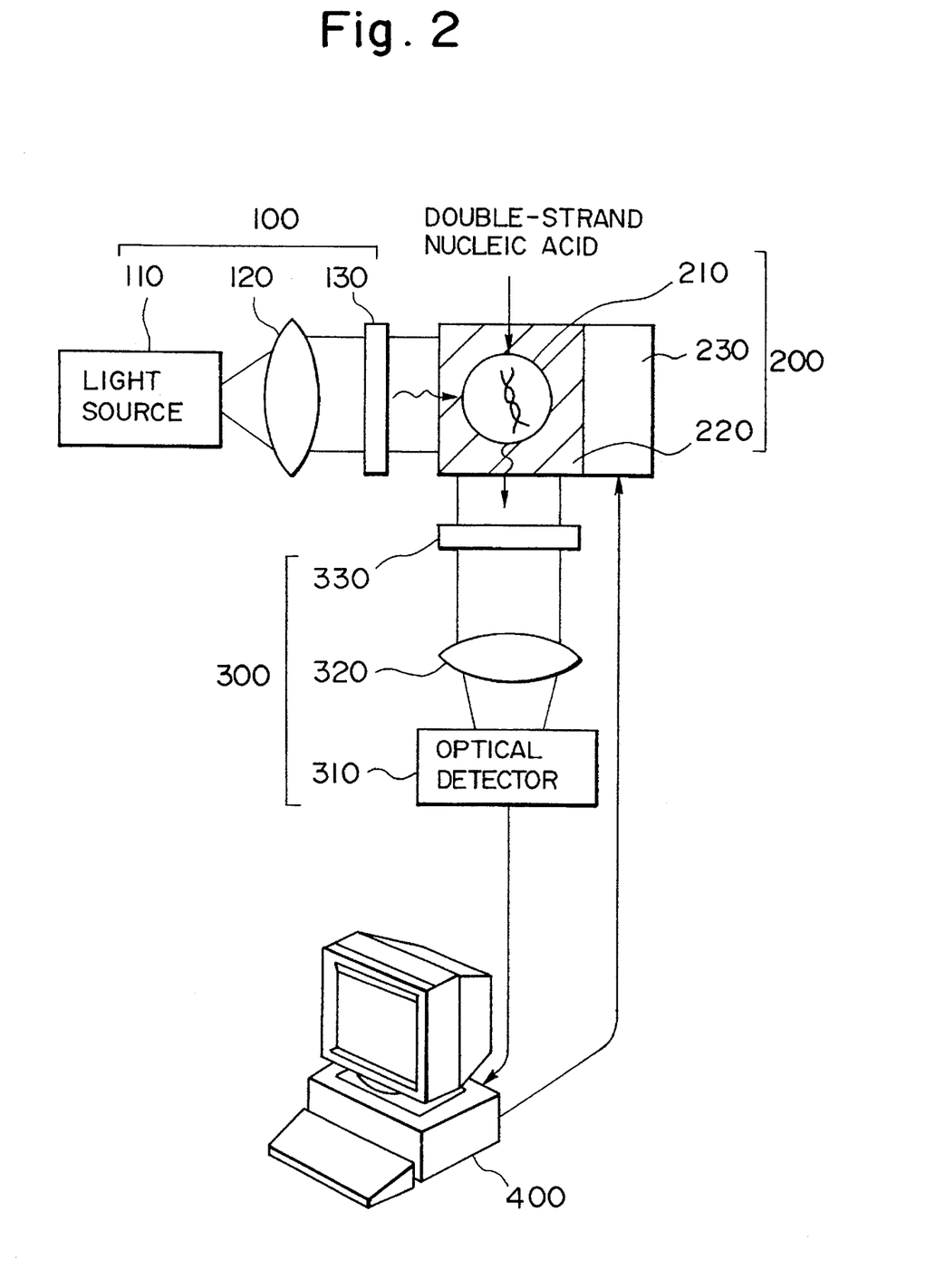
FIG. 2 is a schematic sectional (partially perspective) view showing the structure of a first embodiment of the apparatus for detecting denaturation of a nucleic acid according to the present invention.

FIG. 2 is a schematic view showing the structure of an apparatus for detecting denaturation of a nucleic acid according to a first embodiment of the present invention. In this apparatus, a fluorescein molecule is used as an energy donor and a rhodamine molecule is used as an energy acceptor, and the intensity (or frequency of emission occurrence) of a characteristic fluorescence ($\lambda_A$ fluorescence; wavelength=580 nm) emitted from the rhodamine is measured.

Referring to FIG. 2, this apparatus comprises:

(a) an excitation light irradiation unit 100 for emitting excitation light having a predetermined wavelength to irradiate therewith a double-strand nucleic acid before denaturation and a single-strand nucleic acid after the denaturation (hereinafter, such double-strand and single-strand nucleic acid are comprehensively referred to as "nucleic acid to be measured");

(b) a denaturation condition controlling unit 200 for controlling an environment temperature as a denaturation condition of the nucleic acid to be measured;

(c) a fluorescence detecting unit 300 for detecting fluorescence emitted on the basis of the excitation light irradiation; and (d) a processing unit 400 for receiving, storing and processing a signal supplied from the fluorescence detecting unit 300 which provides an instruction concerning a set temperature to the denaturation condition controlling unit 200.

In FIG. 2, reference numeral 100 denotes an excitation light irradiation unit; 110, a light source; 120, a condenser lens; 130, a filter; 200, a denaturation condition controlling unit; 210, a container for a nucleic acid to be measured; 220, a thermally conducting material; 230, a variable heat source; 300, a fluorescence detecting unit; 310, a photodetector; 320, a condenser leans; 330, a filter; and 400, a processing unit.

The excitation light irradiation unit 100 used herein comprises: (1) a light source 110 for emitting light having a wavelength region including the wavelength of the excitation light, (2) a condenser lens 120 for concentrating the light emitted from the light source 110, and (3) a filter 130 for selectively transmitting light having a wavelength region including the wavelength of excitation light and a wavelength in the neighborhood thereof.

The denaturation condition controlling unit 200 comprises: (1) a container 210 for containing the nucleic acid to be measured, (2) a thermally conducting material 220 enclosing or surrounding the container 210, and (3) a variable heat source 230 for setting the temperature of the thermally conducting material 220 to a predetermined temperature in response to an instruction from outside. A part of the thermally conducting material 220 is made light-transmitting (inclusive of a vacant space or slit) so that the excitation light is incident to the nucleic acid to be measured contained in the container 210 through such a light-transmitting part, and the fluorescence emitted from the nucleic acid to be measured and propagating toward a specific direction is passed through the light-transmitting part. Further, as the variable heat source 230, a heater or the like may be used.

The fluorescence detecting unit 300 comprises: (1) a filter 330 for selectively transmitting light having a wavelength region including the wavelength of the $\lambda_A$ fluorescence and a wavelength in the neighborhood thereof, (2) a condenser lens 320 for concentrating light transmitting through the filter 330, and (3) a photodetector 310 for receiving light passing through the condenser lens 320 to convert the light into an electric signal.

In the apparatus as shown in FIG. 2, denaturation of a nucleic acid may be detected in the following manner.

First, a nucleic acid to be measured is prepared and charged into the container 210. At this time, the set temperature based on the instruction from the processing unit 400 to the denaturation condition controlling unit 200 may be such that it provides a temperature in the container 210 at which the nucleic acid to be measured is not denatured. In this state, the excitation light irradiation unit 100 is driven to supply excitation light to the nucleic acid to be measured. The fluorescein molecule provided to the nucleic acid to be measured which has been irradiated with the excitation light makes a transition to an excited state.

In a case where no rhodamine molecule is present within a distance of 7 nm from the fluorescein molecule in the excited state, the fluorescein molecule emits the characteristic fluorescence ($\lambda_D$ fluorescence; wavelength=520 nm) and makes a transition to the ground state. On the other hand, in a case where a rhodamine molecule is present within a distance of 7 nm from the fluorescein molecule in the excited state, energy is transferred from the fluorescein molecule functioning as an energy donor to the rhodamine molecule functioning as an energy acceptor. When such energy transfer occurs, the fluorescein molecule makes a transition to the ground state without emitting the $\lambda_D$ fluorescence, and the rhodamine molecule makes a transition to the excited state and thereafter makes a transition to the ground state while emitting the $\lambda_A$ fluorescence.

The thus emitted $\lambda_A$ fluorescence is transmitted through the filter 330, and then inputted to the photodetector 310 through the condenser lens 320. The photodetector 310 detects the light upon receipt thereof, and converts it into an electric signal to output the resultant electric signal to the processing unit 400. The processing unit 400 receives a light reception signal supplied from the photodetector 310 and stores the signal together with the above-mentioned set temperature.

Then, the processing unit 400 instructs the denaturation condition controlling unit 200 to change the set temperature to a higher temperature than that in the preceding measurement. In this state, the excitation light irradiation unit 100 is driven to supply excitation light to the nucleic acid to be measured, and the $\lambda_A$ fluorescence emission is measured in the same manner as described above. At this time, the processing unit 400 receives the light reception signal supplied from the photodetector 310 and stores the signal together with the set temperature after the above-mentioned temperature change.

Subsequently, while the set temperature of the denaturation condition controlling unit 200 is successively increased according to instructions given by the processing unit 400, the $\lambda_A$ fluorescence emitted from the nucleic acid is measured at each of set temperatures. The light reception signal supplied from the photodetector 310 under a condition corresponding to each of set temperatures is inputted to the processing unit 400 and stored therein together with the corresponding set temperature.

Figure 3A:
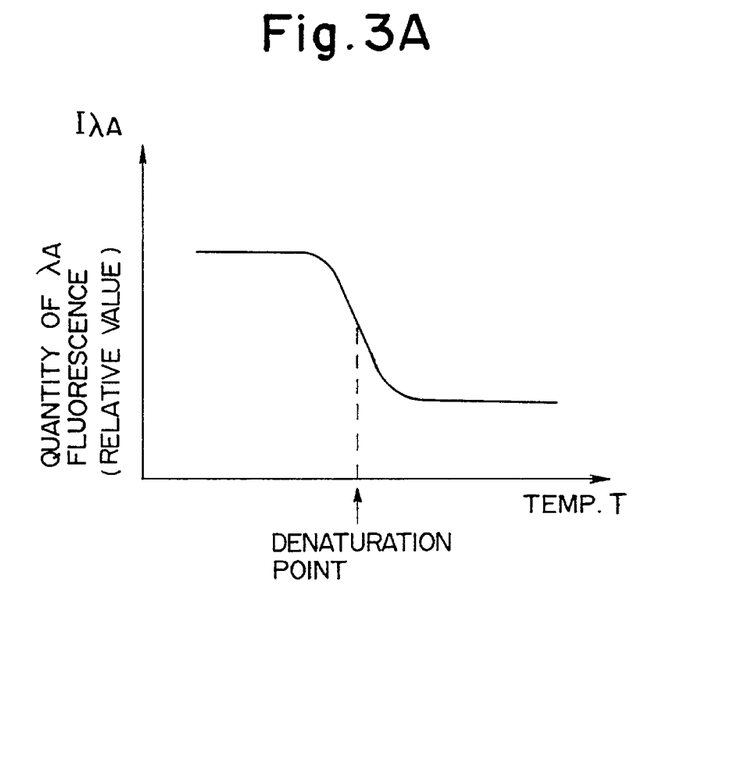
FIGS. 3A and 3B are schematic views for illustrating the detection of a denaturation point utilizing the measurement of a $\lambda_A$ fluorescence (i.e., fluorescence emitted from an energy acceptor) intensity.
Figure 3B:
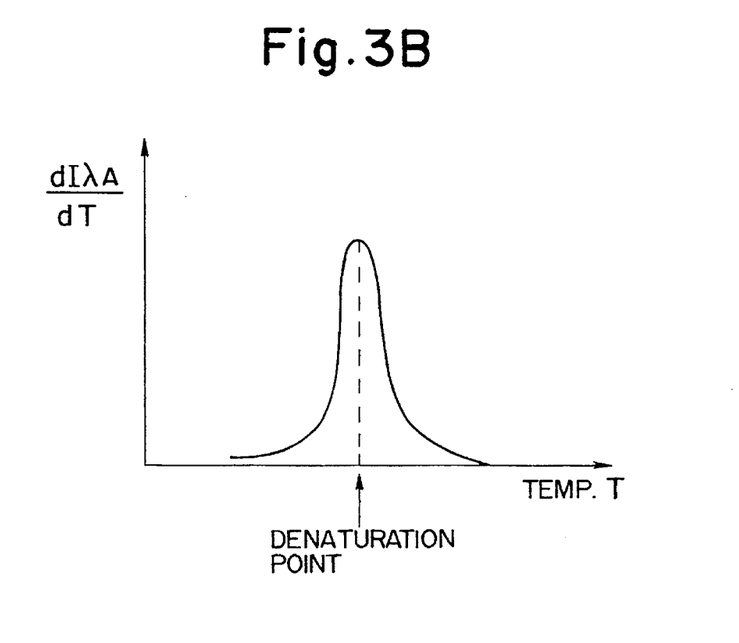

FIGS. 3A and 3B are views each showing results of measurement obtained through the above-mentioned measurement procedure. FIG. 3A is a graph obtained by plotting the contents or data stored in the processing unit 400. In FIG. 3A, the abscissa represents temperature and the ordinate represents the intensity of $\lambda_A$ fluorescence (or frequency of the $\lambda_A$ fluorescence detection). FIG. 3B is a graph obtained by plotting the temperature data (abscissa) and differential value of the $\lambda_A$ fluorescence intensity with respect to temperature (ordinate), on the basis of the data as shown in FIG. 3A.

As shown in FIG. 3A, the $\lambda_A$ fluorescence intensity before the denaturation is stronger than the $\lambda_A$ fluorescence intensity after the denaturation and is abruptly changed at a specific temperature or in the neighborhood thereof. The temperature at which such an abrupt change occurs is detected as a denaturation point. Alternatively, when the differential value of the $\lambda_A$ fluorescence intensity with respect to temperature is calculated on the basis of the above-mentioned stored data, a graph as shown in FIG. 3B may be obtained. In such a case, the denaturation point may also be determined as the largest absolute value of the differential value.

Figure 4A:
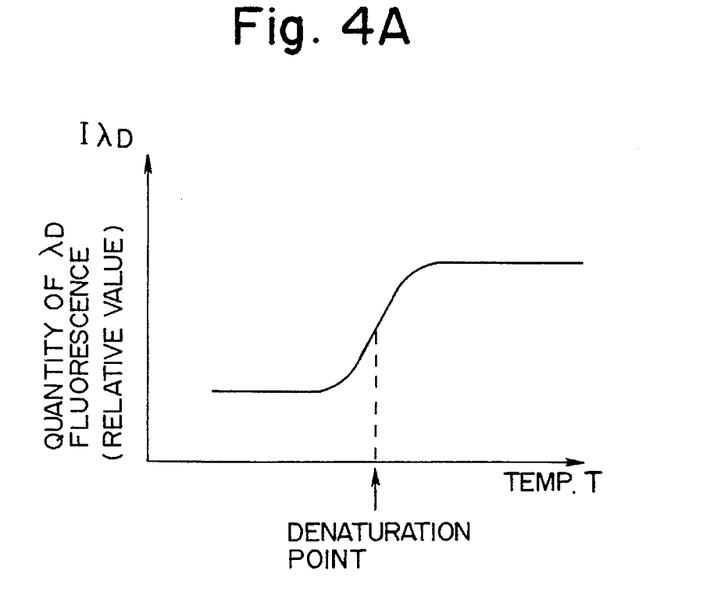
FIGS. 4A and 4B are schematic views for illustrating the detection of a denaturation point utilizing the measurement of a $\lambda_D$ fluorescence (i.e., fluorescence emitted from an energy donor) intensity.
Figure 4B:
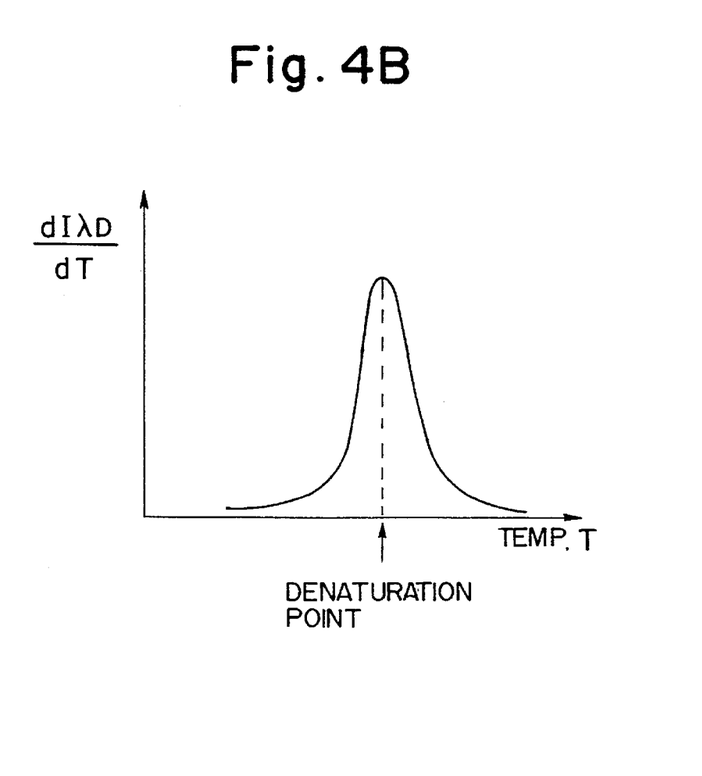

In this embodiment, the value or amount to be measured may also be the intensity of the $\lambda_D$ fluorescence. In such a case, measurement may be conducted in the same manner as described above except for using a filter having a transmittance wavelength band including the wavelength of the $\lambda_D$ fluorescence or in the neighborhood thereof as the filter 330. FIGS. 4A and 4B are views each showing the results of measurement obtained through such a measurement procedure. FIG. 4A is a graph obtained by plotting the contents or data stored in the processing unit 400. In FIG. 4A, the abscissa represents temperature and the ordinate represents the intensity of $\lambda_D$ fluorescence (or frequency of the $\lambda_A$ fluorescence detection). FIG. 4B is a graph obtained by plotting the temperature data (abscissa) and differential value of the $\lambda_D$ fluorescence intensity with respect to temperature (ordinate), on the basis of the data as shown in FIG. 4A.

As shown in FIG. 4A, the $\lambda_D$ fluorescence intensity before the denaturation is weaker than the $\lambda_D$ fluorescence intensity after the denaturation and is abruptly changed at a specific temperature or in the neighborhood thereof. The temperature at which such an abrupt change occurs is detected as a denaturation point. Alternatively, when the differential value of the $\lambda_D$ fluorescence intensity with respect to temperature is calculated on the basis of the above-mentioned stored data, a graph as shown in FIG. 4B may be obtained. In such a case, the denaturation point may also be determined as the largest absolute value of the differential value.

Figure 5A:
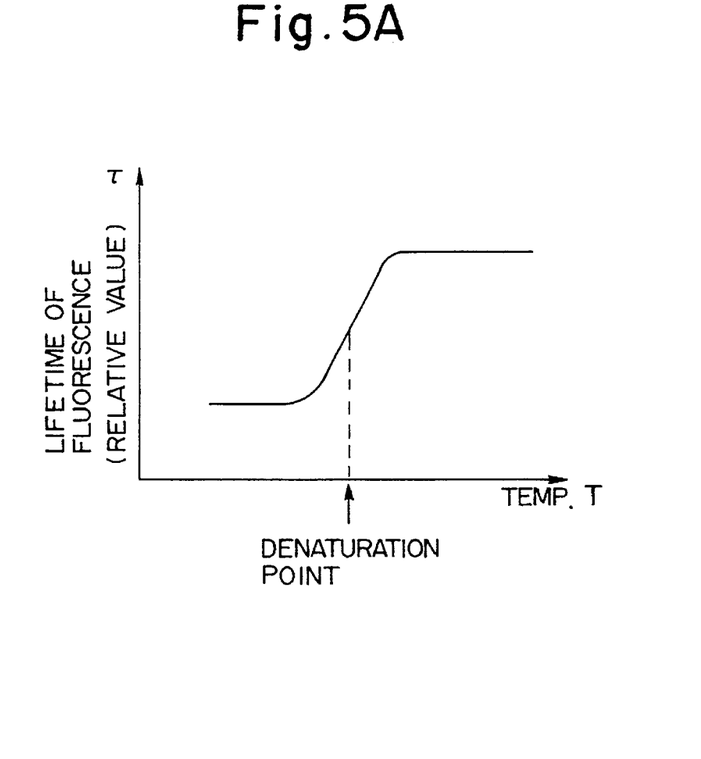
FIGS. 5A and 5B are schematic views for illustrating the detection of a denaturation point utilizing the measurement of fluorescence lifetime.
Figure 5B:
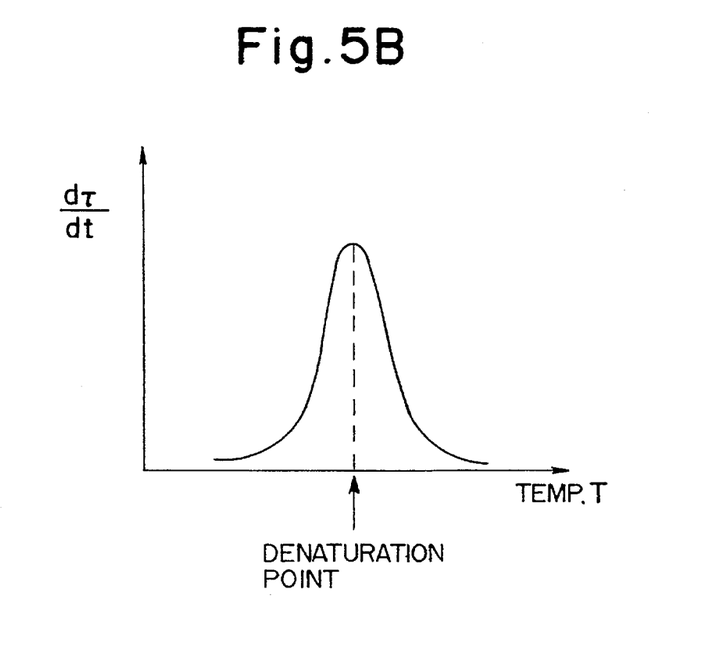

In this embodiment, the value or amount to be measured may also be the lifetime of the fluorescence (e.g., the lifetime of the $\lambda_D$ fluorescence). In such a case, measurement may be conducted in the same manner as described above except that a filter having a transmittance wavelength band including the wavelength of the $\lambda_D$ fluorescence or in the neighborhood thereof is used as the filter 330, and an optical waveform measuring device such as streak camera is used as the photodetector 310. In such a case, the processing unit 400 stores the values of fluorescence lifetime together with the set temperature.

FIGS. 5A and 5B are views each showing the results of measurement obtained through such a measurement procedure. FIG. 5A is a graph obtained by plotting the contents or data stored in the processing unit 400. In FIG. 5A, the abscissa represents temperature and the ordinate represents the lifetime of the fluorescence ($\lambda_D$ fluorescence) emitted from the energy donor. FIG. 5B is a graph obtained by plotting the temperature data (abscissa) and differential value of the lifetime of fluorescence ($\lambda_D$ fluorescence) emitted from the energy donor with respect to temperature (ordinate), on the basis of the data as shown in FIG. 5A.

As shown in FIG. 5A, the average lifetime of the fluorescence before the denaturation is larger than the average lifetime of fluorescence after the denaturation and is abruptly changed at a specific temperature or in the neighborhood thereof. The temperature at which such an abrupt change occurs is detected as a denaturation point. Alternatively, when the differential value of the fluorescence lifetime with respect to temperature is calculated on the basis of the above-mentioned stored data, a graph as shown in FIG. 5B may be obtained. In such a case, the denaturation point may also be determined as the largest absolute value of the differential value.

(Second Embodiment)

Figure 6:
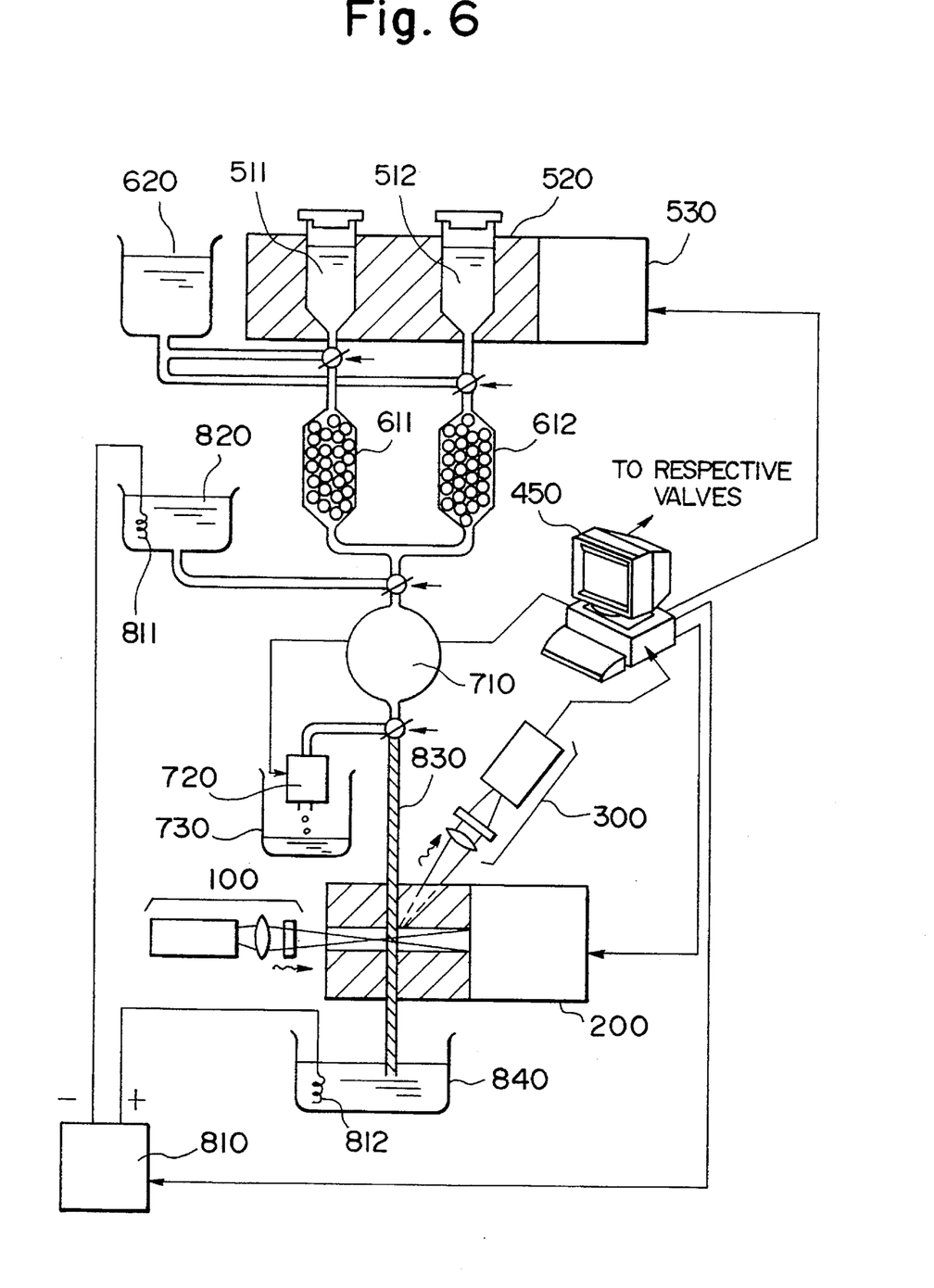
FIG. 6 is a schematic sectional (partially perspective) view showing the structure of a second embodiment of the apparatus for detecting denaturation of a nucleic acid according to the present invention.

FIG. 6 is a schematic view showing the structure of an apparatus for detecting denaturation of a nucleic acid according to a second embodiment of the present invention. In the above-mentioned first embodiment, a nucleic acid prepared in advance is used as the nucleic acid to be measured. On the other hand, an apparatus according to this embodiment is one for detecting denaturation of a nucleic acid to be measured which may be prepared by combining or hybridizing a nucleic acid sample to be examined and a reference (or probe) nucleic acid sample as starting materials. More specifically, in this embodiment, the nucleic acid to be measured comprises the nucleic acid to be examined in a single-strand form and the reference nucleic acid in a single-strand form binding to the nucleic acid to be examined. Similarly as in the first embodiment described above, a fluorescein molecule is used as an energy donor and a rhodamine molecule is used as an energy acceptor.

More specifically, the apparatus according to this embodiment comprises:

(a) a nucleic acid amplifying unit for preparing a sample comprising a predetermined portion of a reference double-strand nucleic acid and a portion a double-strand nucleic acid to be examined which corresponds to the predetermined portion, and then PCR-amplifying one of these double-strand nucleic acids by using a base or nucleotide provided or labeled with a fluorescein molecule, and PCR-amplifying the other of these double-strand nucleic acids by using a base provided with a rhodamine molecule;

(b) an extracting unit for extracting, with respect to these two species of the double-strand nucleic acids amplified by the above-mentioned nucleic acid amplifying unit, a single-strand nucleic acid forming one of the two species of double-strand nucleic acids, and a single-strand nucleic acid which is in a complementary relation with the above-mentioned single-strand nucleic acid from the other of the two species of double-strand nucleic acids;

(c) a mixing unit for receiving the two species of the single-strand nucleic acids extracted by the extracting unit and mixing the two species of the single-strand nucleic acids to produce a nucleic acid to be measured while mixing the nucleic acid to be measured with a gel carrier;

(d) a gel electrophoresis unit for leading or introducing the nucleic acid to be measured produced by the mixing unit to a measurement point;

(e) an excitation light irradiation unit 100 for emitting excitation light having a predetermined wavelength to irradiate a double-strand nucleic acid before denaturation or a single-strand nucleic acid after the denaturation, with the excitation light;

(f) a denaturation condition controlling unit 200 for controlling an environment temperature of the nucleic acid to be measured as a denaturation condition;

(g) a fluorescence detection unit 300 for detecting fluorescence emission based on the irradiation of the nucleic acid with the excitation light; and (h) a processing unit 450 for giving an instruction for a set temperature to the denaturation condition control unit 200 to control the operation of the entire apparatus, and for receiving, storing and processing a signal supplied from the fluorescence detecting unit 300.

In FIG. 6, reference numeral 450 denotes a processing unit; 511, 512, containers for PCR-amplification; 520, a thermally conducting unit; 530, a variable heat source; 611, 612, containers for absorbing materials; 620, a container for an eluent denaturant; 710, a mixing vessel; 720, a pump; 730, a container for discharged solution; 810, a power source; 811, 812, electrodes; 820, 840, containers for a gel carrier; and 830, a column.

The above-mentioned nucleic acid amplifying unit comprises: (1) a container 511 for containing a reference nucleic acid sample and a base provided with a fluorescein molecule, (2) a container 512 for containing a nucleic acid to be examined and a base provided with a rhodamine molecule, (3) a thermally conducting material 520 for surrounding or enclosing the containers 511 and 512, and (4) a variable heat source 530 for setting the temperature of the thermally conducting material 520 to a designated temperature in response to an instruction from outside.

The extracting unit comprises: (1) a container 611 connected to the container 511 through a valve, for containing a matrix material having a surface to which avidin is attached, (2) a container 612 connected to the above container 512 through a valve, for containing a matrix material having a surface to which the avidin is attached, and (3) a container 620 connected to the above container 611 and container 612 through respective valves, for containing formamide (80%) which is an extracting solution having a function of a denaturant or denaturing agent.

The mixing unit comprises: (1) a mixing vessel 710 connected to the above container 611 and container 612 through respective valves, for mixing the two species of extracted single-strand nucleic acids, (2) a pump 720 connected to the mixing vessel 710 through a valve, for discharging a solution in the mixing vessel 710, and (3) a container 730 for containing the solution discharged from the pump 720.

The gel electrophoresis unit comprises: (1) a power supply 810 for supplying an application voltage, (2) a negative electrode 811 connected to the power supply 810, (3) a positive electrode 812 connected to the power supply 810, (4) a container 820 connected to the mixing vessel 710 through a valve, for containing a gel carrier, (5) a column 830 in a capillary or slender tube form, one end of which is connected to the mixing vessel 710 through a valve, and (6) a container 840 disposed in the other end side of the column 830, for containing the gel carrier.

In this embodiment, the excitation light irradiation unit 100, the denaturation condition controlling unit 200 and the fluorescence detecting unit 300 have the same structure or constitution as those constituting the first embodiment as described above. The processing unit 450 has, in addition to the components constituting the processing unit 400 in the first embodiment, an amplification controlling function to give an instruction for a set temperature to the nucleic acid amplifying unit and a function of controlling the valves disposed in the apparatus, and supplies control signals to these components (inclusive of the valves).

Figure 7:
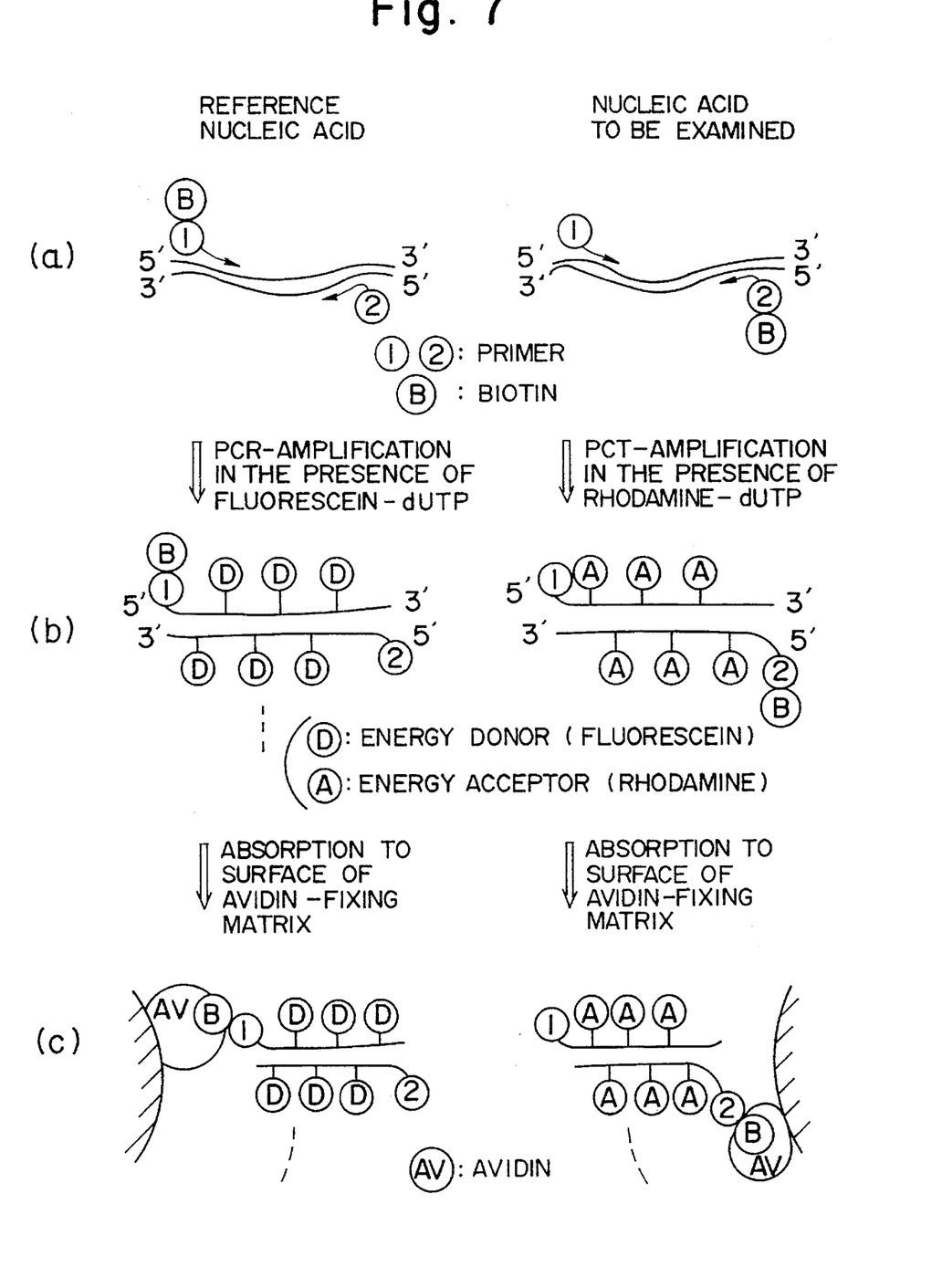
FIG. 7 is a schematic view for illustrating a method (former stage) of preparing a double-strand nucleic acid to be measured.
Figure 8:
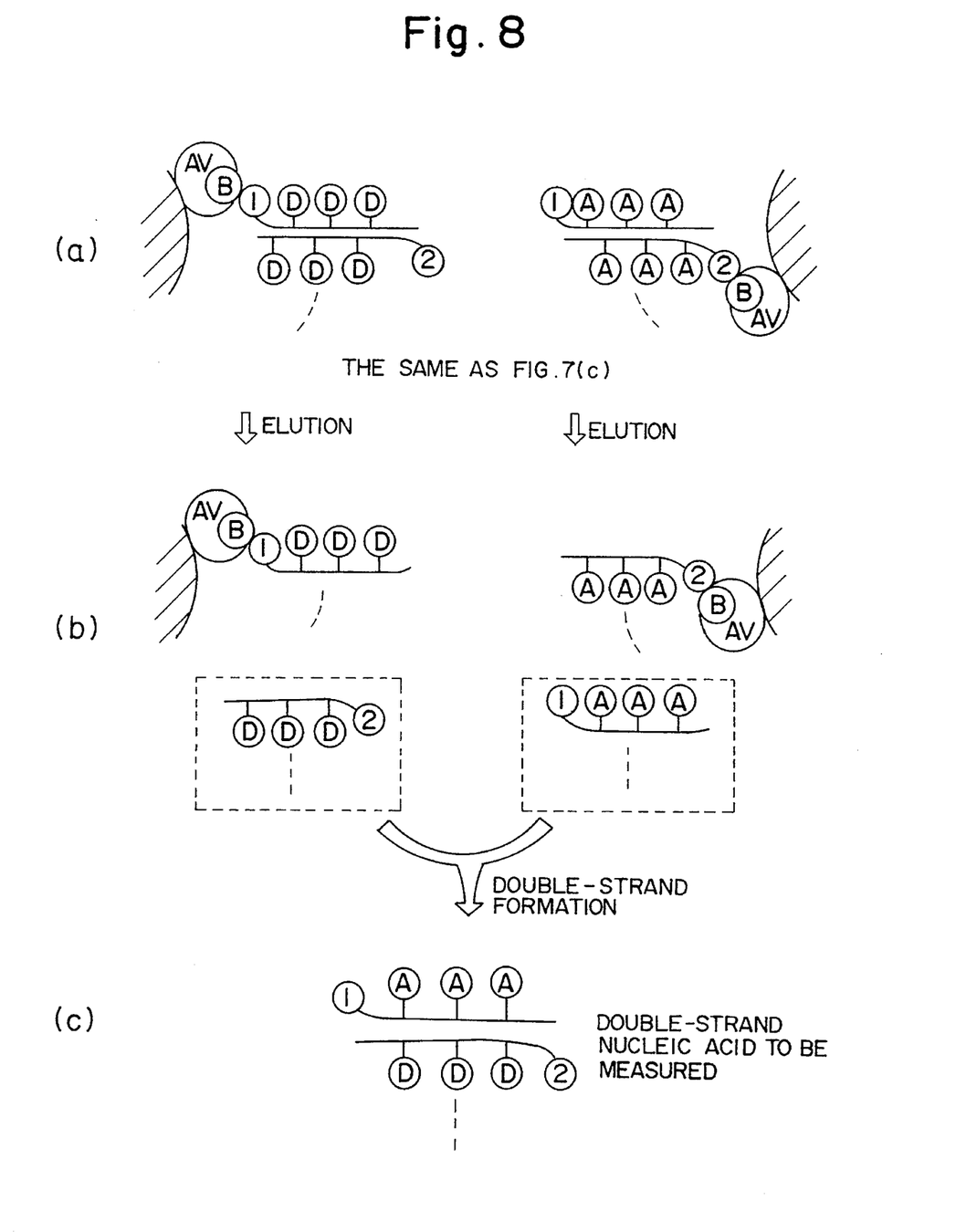
FIG. 8 is a schematic view for illustrating a method (latter stage) of preparing a double-strand nucleic acid to be measured.

In the apparatus shown in FIG. 6, first, a nucleic acid to be measured is prepared. FIGS. 7 and 8 are schematic views for illustrating a procedure for preparing a nucleic acid to be measured from a reference nucleic acid sample and a nucleic acid sample to be examined. With reference to these Figures, operation of preparing the nucleic acid to be measured is described below.

Referring to FIG. 7(a), two species of primers are respectively caused to contact the reference nucleic acid and the nucleic acid to be examined to produce a reference nucleic acid sample and a nucleic acid sample to be examined respectively including predetermined sites. At this time, biotin is provided to one of these primers to bind to the reference nucleic acid and biotin is provided to the other of these primers to bind to the nucleic acid to be examined.

With respect to the thus produced samples, the reference nucleic acid sample is subjected to PCR-amplification in the container 511 containing a solution comprising fluorescein-dUTP, and the nucleic acid sample to be examined is subjected to PCR-amplification in the container 512 containing a solution comprising rhodamine-dUTP, respectively, under temperature control using the variable heat source 530 controlled by the processing unit 450 through the thermally conducting material 520. As a result, there are produced a large amount of reference nucleic acid comprising a base provided with the fluorescein and the nucleic acid to be examined composing a base provided with the rhodamine, as shown in FIG. 7(b).

Each of the amplified nucleic acids is introduced into the container 611 or the container 612 under valve control conducted by the processing unit 450. At this time, a predetermined site provided with the biotin is coupled with the avidin provided to the matrix material preliminarily contained in the container 611 and 612, and remains in the containers 611 and 612. However, the other component not provided with the biotin is passed through the containers 611 and 612, as shown in FIG. 7(c) and FIG. 8(a). The solution having passed through the containers is stored in the mixing vessel 710 and then discharged through the pump 720 to the container 730 in response to an instruction from the processing unit 450.

Then, the formamide (80%) is introduced into the containers 611 and 612 from the container 620, and a single-strand nucleic acid at the primer side not provided with the biotin is eluted as shown in FIG. 8(b). The eluted single-strand nucleic acid is introduced into the mixing vessel 710 under valve control conducted by the processing unit 450, and is subjected to annealing after the mixing, thereby to provide a nucleic acid to be measured, as shown in FIG. 8(c). At this time, the gel carrier is introduced into the mixing vessel 710 and the column 830.

Under the application of a voltage from the power supply 810, the nucleic acid to be measured is moved through the mixing vessel 710 and the column 830 to the measurement point where the denaturation condition controlling unit 200 is disposed. Subsequently, the characteristic fluorescence from the nucleic acid is measured in the same manner as in the first embodiment as described above, thereby to detect the denaturation thereof.

The present invention is not limited to the above mentioned specific embodiments but various modifications thereto may also be possible. For example, while temperature is used as the denaturation condition in the above-mentioned embodiments, the concentration of a denaturing agent such as formamide may also be a denaturation condition and such a concentration may be changed gradually or stepwise. In addition, the energy donor and the energy acceptor are not limited to a combination of fluorescein and rhodamine. Alternatively, such a combination of an energy donor and an energy acceptor having different characteristic fluorescence wavelength may be used as long as energy transfer occurs therebetween. In addition, the method of preparing the nucleic acid to be measured in the second embodiment is an example, and any of other known methods for the preparation of a nucleic acid to be measured may also be used.

As described hereinabove, when the apparatus for detecting denaturation of a nucleic acid according to the first embodiment of the present invention is used, the characteristic fluorescence of a fluorescent molecule provided to a nucleic acid is measured while controlling the denaturation condition at a measurement point in a quasi-static manner, and therefore it is not necessary to conduct electrophoresis in a gel carrier provided with a gradient of denaturation condition. As a result, the denaturation of the nucleic acid can be detected more rapidly with a higher accuracy.

In addition, when the apparatus for detecting denaturation of a nucleic acid according to the second embodiment of the present invention is used, a nucleic acid to be measured is prepared by using a reference nucleic acid sample and a nucleic acid sample to be examined as starting materials, and then fluorescence is measured in the same manner as in the apparatus according to the first embodiment. As a result, measurement can be conducted more effectively in a through or successive mode.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application No. 175730/1993 filed on Jul. 15, 1993 is hereby incorporated by reference.

What is claimed is:

1. An apparatus for detecting denaturation of a nucleic acid, comprising:

first nucleic acid amplifying means for separating a predetermined site of a first double-stranded nucleic acid to be examined into a first single-stranded nucleic acid and a second single-stranded nucleic acid and producing a plurality of a third single-stranded nucleic acid and a fourth single-stranded nucleic acid, said third single-stranded nucleic acid comprising a base or nucleotide provided with a first label molecule and having a base sequence complementary to that of the first single-stranded nucleic acid, said fourth single-stranded nucleic acid having a base sequence complementary to that of the second single-stranded nucleic acid;

second nucleic acid amplifying means for separating a predetermined site of a second double-stranded nucleic acid as a reference, which is the same or substantially the same as the first double-strand nucleic acid, into a fifth single-stranded nucleic acid which is the same or substantially the same as the first single-stranded nucleic acid, and a sixth single-stranded nucleic acid which is the same as or substantially the same as the second single-stranded nucleic acid, and produceing a plurality of a seventh single-stranded nucleic acid and an eighth single-stranded nucleic acid; said seventh single-stranded nucleic acid comprising a base or nucleotide provided with a second label molecule which is capable of causing energy transfer between itself and the first label molecule located within a predetermined distance, and having a base sequence complementary to that of the fifth single-stranded nucleic acid; said eighth single-stranded nucleic acid having a base sequence complementary to that of the sixth single-stranded nucleic acid;

nucleic acid mixing means for mixing the third single-stranded nucleic acid and the eighth single-stranded nucleic acid after the extraction thereof to produce a third double stranded or partially double-stranded nucleic acid;

denaturation condition controlling means for controlling a condition for denaturation under which the third double-stranded nucleic acid is separated into the third single-stranded nucleic acid and the eighth single-stranded nucleic acid;

irradiation means for emitting excitation light having a predetermined wavelength to irradiate the third double-stranded nucleic acid before denaturation by the denaturation controlling means, and the third single-stranded nucleic acid and eighth single-stranded nucleic acid after denaturation by the denaturation controlling means;

fluorescence detection means for detecting fluorescence emission based on the excitation light irradiation which emission is capable of being changed depending on a change in the amount of energy transfer between the first label molecule and the second label molecule, whereby a denaturation point is determined on the basis of the change in the fluorescence emission in response to the change in the denaturation condition; and processing means for receiving, storing and processing a signal supplied from the fluorescence detection means;

whereby the fluorescence emitted from the nucleic acid is observed while changing the denaturation condition by the denaturation condition controlling means to measure the denaturation condition of the third double-stranded nucleic acid.

2. An apparatus for detecting denaturation of a nucleic acid according to claim 1, wherein the nucleic acid mixing means mixes the third single-stranded nucleic acid and the eighth single-stranded nucleic acid nucleic acid after the extraction thereof.

3. An apparatus for detecting denaturation of a nucleic acid according to claim 1, wherein the denaturation condition is temperature and the denaturation condition controlling means comprises a temperature controller.

4. An apparatus for detecting denaturation of a nucleic acid according to claim 1, wherein the denaturation condition is hydrogen ion concentration and the denaturation condition controlling means comprises a hydrogen ion concentration controller.

5. An apparatus for detecting denaturation of a nucleic acid according to claim 1, wherein the denaturation condition is the concentration of a denaturing agent capable of denaturing the third double-strand nucleic acid and the denaturation condition controlling means comprises a denaturing agent concentration controller.

6. An apparatus for detecting denaturation of a nucleic acid according to claim 1, wherein the fluorescence detection means selectively detects a first fluorescence signal which is emitted from the first label molecule and is capable of being changed depending on a change in the amount of energy transfer between the first label molecule and the second label molecule, and the processing means calculates a denaturation point on the basis of the change in the first fluorescence signal in response to the change in the denaturation condition.

7. An apparatus for detecting denaturation of a nucleic acid according to claim 1, wherein the fluorescence detection means selectively detects a second fluorescence signal which is emitted from the second label molecule and is capable of being changed depending on a change in the amount of energy transfer between the first label molecule and the second label molecule, and the processing means calculates a denaturation point on the basis of the change in the second fluorescence signal in response to the change in the denaturation condition.

8. An apparatus for detecting denaturation of a nucleic acid according to claim 1, wherein the fluorescence detection means detects the lifetime of fluorescence which is capable of being changed depending on a change in the amount of energy transfer between the first label molecule and the second label molecule, and the processing means calculates a denaturation point on the basis of the change in the lifetime of the fluorescence in response to the change in the denaturation condition.

9. An apparatus for detecting denaturation of a nucleic acid according to claim. 1, wherein the fluorescence detection means detects the spectrum of fluorescence which is capable of being changed depending on a change in the amount of energy transfer between the first label molecule and the second label molecule, and the processing means calculates a denaturation point on the basis of the change in the spectrum of the fluorescence in response to the change in the denaturation condition.

10. An apparatus for detecting denaturation of a nucleic acid according to claim 9, wherein the fluorescence detection means comprises a fluorescence spectrum measuring device.

11. An apparatus for detecting denaturation of a nucleic acid according to claim 10, wherein the fluorescence detection means comprises a fluorescence spectrum measuring device of a time-resolved type.

* * * * *